(12) United States Patent
Chen et al.

(10) Patent No.: US 12,588,807 B2
(45) Date of Patent: Mar. 31, 2026

(54) VISION TEST APPARATUS, METHOD AND SYSTEM AND NON-TRANSIENT COMPUTER READABLE RECORDING MEDIUM

(71) Applicant: EYEMIKAN BIOTECH INC., Taipei City (TW)

(72) Inventors: Ming-Fu Chen, Taipei City (TW); Cheng-Hsiung Chen, Taipei City (TW)

(73) Assignee: EYEMIKAN BIOTECH INC., Taipei City (TW)

( * ) Notice: Subject to any disclaimer, the term of this patent is extended or adjusted under 35 U.S.C. 154(b) by 778 days.

(21) Appl. No.: 17/857,843

(22) Filed: Jul. 5, 2022

(65) Prior Publication Data

US 2023/0024546 A1     Jan. 26, 2023

(30) Foreign Application Priority Data

Jul. 16, 2021    (TW) ................................. 110126315

(51) Int. Cl.
| | |
|---|---|
| *A61B 3/028* | (2006.01) |
| *A61B 3/00* | (2006.01) |
| *A61B 3/08* | (2006.01) |

(52) U.S. Cl.
CPC ................ *A61B 3/028* (2013.01); *A61B 3/08* (2013.01); *A61B 3/0041* (2013.01)

(58) Field of Classification Search
CPC ......... A61B 3/032; A61B 3/14; A61B 3/0025; A61B 3/028; A61B 3/036; A61B 3/1035;

A61B 3/0008; A61B 3/024; A61B 3/005; A61B 3/08; A61B 3/132; G02B 9/10; G02B 9/14; G02B 9/58; G02B 13/003;
(Continued)

(56) References Cited

U.S. PATENT DOCUMENTS

| | | | | | |
|---|---|---|---|---|---|
| 2009/0244486 A1* | 10/2009 | Oda | ........................ | A61B 3/032 351/240 | |
| 2015/0374233 A1* | 12/2015 | Zhang | ...................... | A61B 3/14 351/246 | |

(Continued)

FOREIGN PATENT DOCUMENTS

| | | | | |
|---|---|---|---|---|
| CN | 2348775 Y | | 11/1999 | |
| CN | 107157437 A | * | 9/2017 | |

(Continued)

*Primary Examiner* — Bumsuk Won
*Assistant Examiner* — Samanvitha Sridhar
(74) *Attorney, Agent, or Firm* — HDLS IPR SERVICES; Chun-Ming Shih

(57) ABSTRACT

A vision test apparatus includes a hollow housing, a converging lens, and a diverging lens. The converging lens is arranged in the hollow housing, and includes a converging focal length. The diverging lens is arranged in the hollow housing at intervals relative to the converging lens, and includes a diverging focal length. Two optical axes of the diverging lens and the converging lens are overlap each other, and the diverging focal length partially overlaps the converging focal length. One end of the hollow housing adjacent to the diverging lens attaches a test optotype displayed by a display apparatus. The diverging lens demagnifies the test optotype to form a first virtual image within the converging focal length. The converging lens magnifies the first virtual image to form a second virtual image for a vision testing.

5 Claims, 8 Drawing Sheets

(58) Field of Classification Search
CPC .............. G02B 13/0035; G02B 13/004; G02B
15/143505; G02B 15/144101
See application file for complete search history.

(56)                References Cited

U.S. PATENT DOCUMENTS

| | | | |
|---|---|---|---|
| 2019/0125179 A1 | 5/2019 | Xu et al. | |
| 2020/0397285 A1 * | 12/2020 | Ralston .............. | G01B 9/02027 |
| 2023/0075963 A1 * | 3/2023 | Arita ................... | A61B 3/0091 |

FOREIGN PATENT DOCUMENTS

| | | | |
|---|---|---|---|
| CN | 110764227 A | 2/2020 | |
| EP | 2901919 A1 * | 8/2015 | ........... A61B 3/1025 |

* cited by examiner

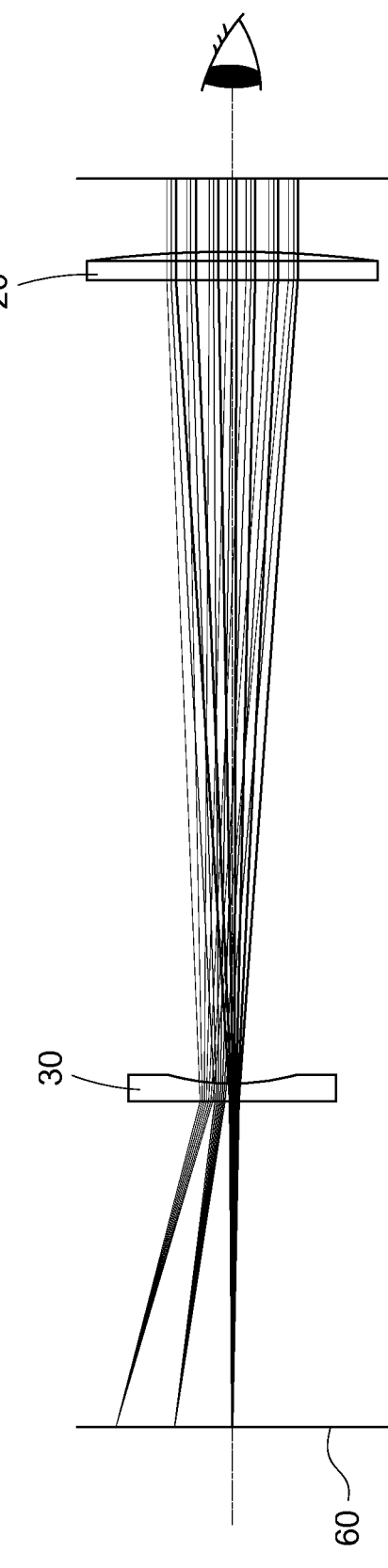
FIG.3

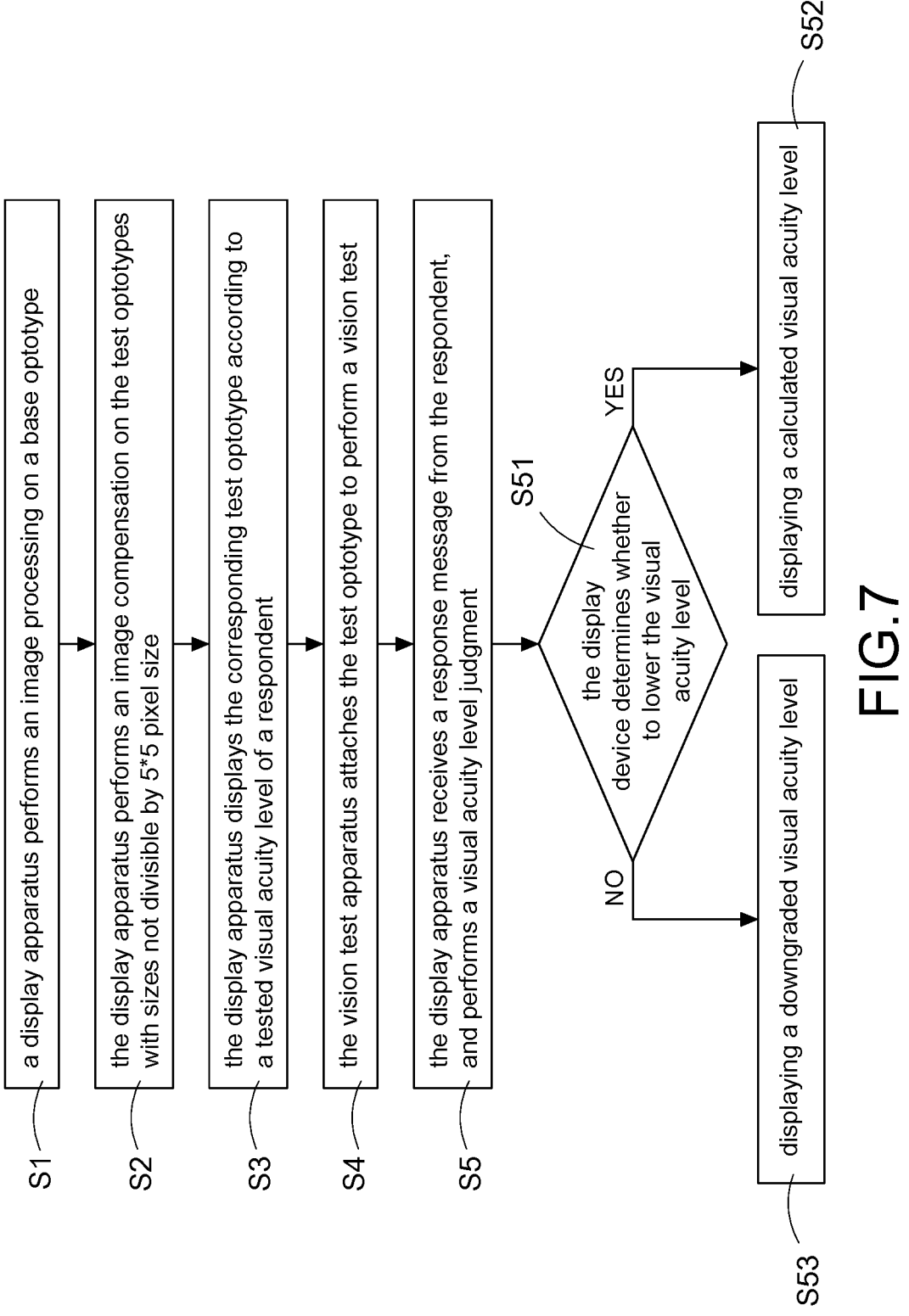

S1 — a display apparatus performs an image processing on a base optotype

S2 — the display apparatus performs an image compensation on the test optotypes with sizes not divisible by 5*5 pixel size S3 — the display apparatus displays the corresponding test optotype according to a tested visual acuity level of a respondent S4 — the vision test apparatus attaches the test optotype to perform a vision test S5 — the display apparatus receives a response message from the respondent, and performs a visual acuity level judgment S51 — the display device determines whether to lower the visual acuity level NO — displaying a downgraded visual acuity level — S53

YES — displaying a calculated visual acuity level — S52

FIG.7

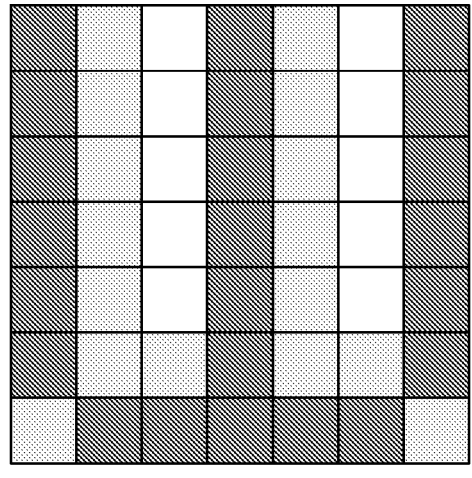
obj1:7x7
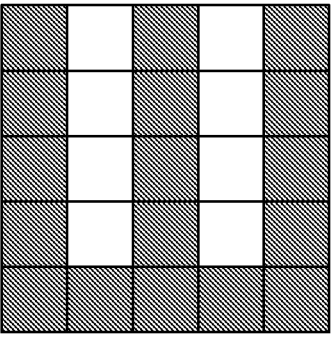
obj1:5x5
FIG.8

VISION TEST APPARATUS, METHOD AND SYSTEM AND NON-TRANSIENT COMPUTER READABLE RECORDING MEDIUM

BACKGROUND

Technical Field

The present disclosure relates to a visual test technology, in particular to a vision test apparatus, a method, a system, and a non-transitory computer-readable recording medium.

Description of Related Art

With the development of electronic apparatuses gradually toward multi-function and easy portability, the time to use electronic apparatuses is getting longer and longer. Further, the age of starting to use electronic apparatuses is getting younger and younger, and the problem of myopia in teenagers is getting worse. After suffering from myopia, visual fatigue is easy to occur. If the myopia is not corrected, there will be symptoms such as inattention and dizziness when looking at objects for a long time. Excessive severity of myopia also increases the risk of eye disease. Therefore, in an early stage of myopia or short-term vision loss caused by visual fatigue, it is very important to detect the changes in visual acuity level in real time, and very important to the health of your eyes.

However, if someone wants to know their vision condition at present, most people go to a professional vision and optical inspection institution such as a hospital or an eyeglass shop, and use professional equipment such as a computer optometrist for optometry. It takes a considerable amount of time, transportation costs and testing fees to go to the inspection institution for each test, so that the visual respondent may difficult to know a changing trend of the visual acuity level at any time.

Therefore, the technical problem of how to reduce or eliminate the time, transportation costs, and testing costs for visual respondent, and how to know easily a changing trend of the visual acuity level at any time, it is an important subject studied by the inventor of the present disclosure.

SUMMARY

An embodiment of the present disclosure relates to a vision test apparatus, which includes a hollow housing, a converging lens, and a diverging lens. The converging lens is arranged in the hollow housing, and includes a converging focal length. The diverging lens is arranged in the hollow housing at intervals relative to the converging lens, and includes a diverging focal length. Two optical axes of the diverging lens and the converging lens are overlap each other, and the diverging focal length partially overlaps the converging focal length. One end of the hollow housing adjacent to the diverging lens attaches a test optotype displayed by a display apparatus. The diverging lens demagnifies the test optotype to form a first virtual image within the converging focal length. The converging lens magnifies the first virtual image to form a second virtual image for a vision testing.

Another embodiment of the present disclosure relates to a binocular vision test apparatus, which includes two vision test apparatuses, and an auxiliary frame. each vision test apparatus includes a first clamping structure in a periphery of the hollow housing. The auxiliary frame includes a second clamping structure, the auxiliary frame engages with the first clamping structure by the second clamping structure to combine with the two vision test apparatuses.

Another embodiment of the present disclosure relates to a method of vision test cooperated with the vision test apparatus to perform the vision testing. The method includes the following steps: a display apparatus performs an image processing on a base optotype with a predetermined pixel size by a scaling method, and the display apparatus generates a plurality of test optotypes with sizes of integral multiple of a 5*5 pixel size and with sizes not divisible by the 5*5 pixel size; the display apparatus performs an image compensation on the test optotypes with sizes not divisible by the 5*5 pixel size, so that the pixel size is between each test optotype with an arithmetic sequence relationship; the display apparatus displays the corresponding test optotype according to a tested visual acuity level of a respondent; the vision test apparatus attaches the test optotype to perform a vision test; and the display apparatus receives a response message from the respondent, and performs a visual acuity level judgment.

Another embodiment of the present disclosure relates to a non-transitory computer-readable recording medium for storing a program to execute the method of vision test cooperated with the vision test apparatus to perform the vision testing when the display apparatus loads the program.

Another embodiment of the present disclosure relates to a vision test system includes the vision test apparatus in the foregoing embodiments, and a display apparatus for executing the method of vision test in the foregoing embodiments.

Therefore, the vision test apparatus, method, system, and non-transitory computer-readable recording medium disclosed in the present disclosure solves the problems of related art that require a fixed field, are inconvenient to carry, and may not easily and instantly to know a changing trend of the visual acuity level at any time. The present disclosure achieves an object of not requiring the fixed field, being portable, and being able to know easily a changing trend of the visual acuity level at any time.

Further, the present disclosure performs the image processing on the base optotype, and generates the plurality of test optotypes with the sizes of integral multiple of the pixel size; and performs the image compensation on the test optotypes with sizes not divisible by the 5*5 pixel size. The present disclosure effectively reduces a high requirement for a resolution of the display apparatus, and the vision test apparatus may be applied to the display apparatus with different resolution levels.

BRIEF DESCRIPTION OF DRAWINGS

FIG. 3 is a schematic diagram of a light path of the vision test apparatus of the present disclosure.

FIG. 7 is a schematic flowchart of a method of vision test of the present disclosure.

FIG. 8 is a schematic diagram of performing an image compensation on a test optotype of the method of vision test of the present disclosure.

DETAILED DESCRIPTION

Figure 1:
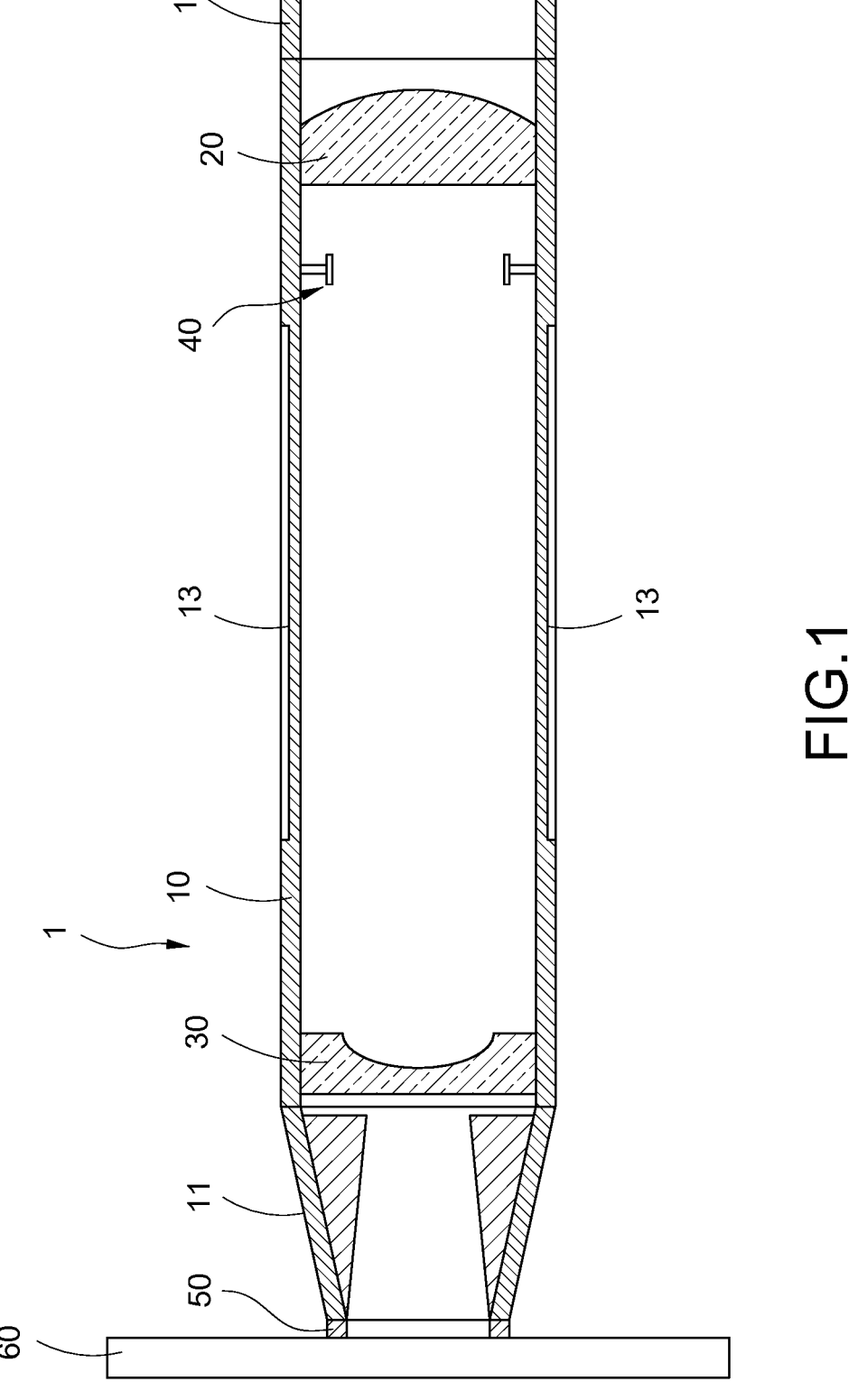
FIG. 1 is a schematic structural diagram of a first embodiment of a vision test system and a vision test apparatus.

Please refer to FIG. 1, which is a schematic structural diagram of a first embodiment of a vision test system and a vision test apparatus 1. The vision test system includes the vision test apparatus 1 and a display apparatus 60. The display apparatus 60 includes a smart mobile phone, a personal digital assistant, a tablet computer, and other electronic devices with a display screen. The vision test apparatus includes a hollow housing 10, a light shield 11, a visual tube 12, a converging lens 20, a diverging lens 30 and a diaphragm 40. During a vision test, the vision test apparatus 1 is attached to the display apparatus 60 for a vision testing. The hollow housing 10 is made of translucent or transparent materials, so that the hollow housing 10 allows an external ambient light to penetrate into the vision test apparatus 1, so that the vision test apparatus 1 receives the external ambient light to meet an illumination requirement of an indoor space during the vision testing.

The light shield 11 is connected to one end of the hollow housing 10, and is adjacent to the diverging lens 30. The light shield 11 has a tapered structure and tapers toward the diverging lens. The light shield 11 keeps a fixed distance such as 30 mm between the diverging lens 30 and a display screen of the display apparatus 60, and the light shield 11 is used to eliminate reflected or refracted lights. When necessary, an inner surface of the light shield 11 is further provided with specific textures such as stepped shapes, sandblasted multiple concave-convex shapes, etc., to roughen the inner surface and enhance an effect of eliminating reflected or refracted lights. The visual tube 12 is connected to the other end of the hollow housing 10 and is adjacent to the converging lens 20. The visual tube 12 is used for keeping a fixed distance between eyes of a respondent and the converging lens 20.

Further, in the first embodiment of the present disclosure, in order to make the vision test apparatus 1 stably attached to a display area of the display apparatus 60, a periphery of an opening at one end of the light shield 11 includes an attachment layer 50. The attachment layer 50 includes any one of a silicone layer, an electrostatic glass sticker, and a chemical adhesive layer. The silicone layer has high friction resistance, the electrostatic glass sticker has electrostatic adsorption properties, and the chemical adhesive layer has an adhesive. Therefore, the vision test apparatus 1 has a stable adhesion force, and has an attachable/detachable effect for repeated use.

Figure 2:
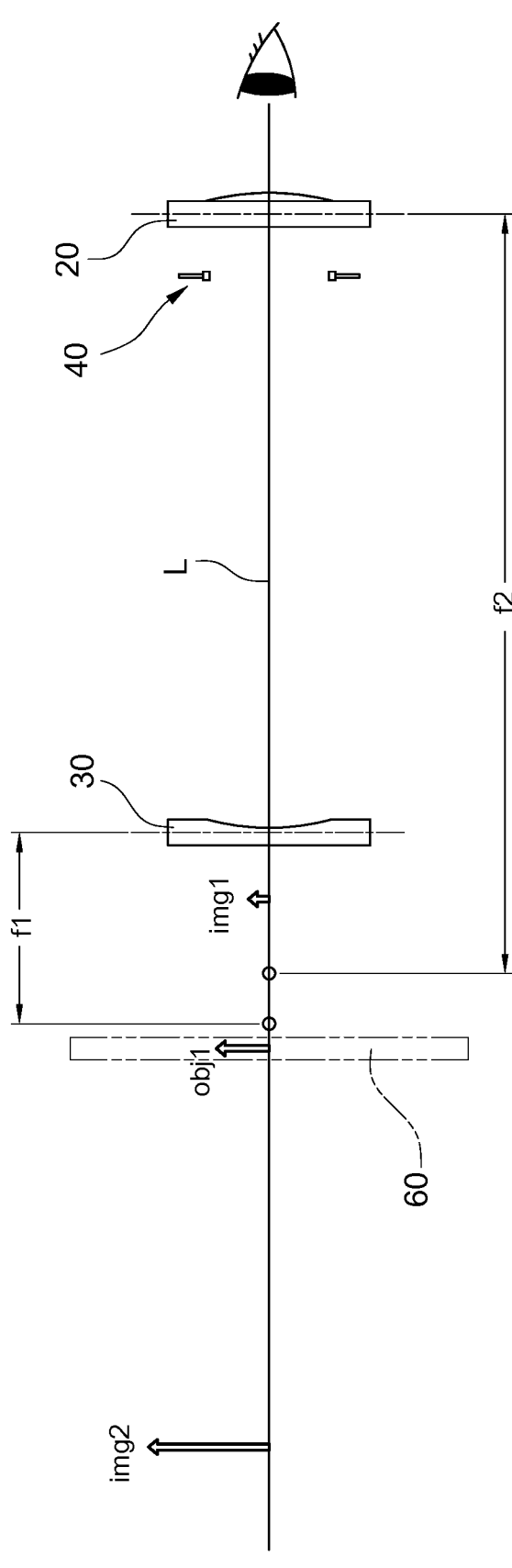
FIG. 2 is an imaging schematic diagram of the system of the vision test apparatus of the present disclosure.

Please refer to FIG. 2 and FIG. 3. FIG. 2 is an imaging schematic diagram of the system of the vision test apparatus of the present disclosure. FIG. 3 is a schematic diagram of a light path of the vision test apparatus of the present disclosure. The converging lens 20 is arranged in the hollow housing 10, and includes a converging focal length f2. The diverging lens 30 is arranged in the hollow housing 10 at intervals relative to the converging lens 20, and includes a diverging focal length f1. In order to increase a range of tested visual acuity levels of the vision test apparatus 1 of the present disclosure, two optical axes L of the diverging lens 30 and the converging lens 20 are overlapped each other in the hollow housing 10, and the diverging focal length f1 is partially overlapped with the converging focal length f2.

During a vision test, the display apparatus 60 is activated, a test optotype obj1 is displayed, and the attachment layer 50 of the light shield 11 is attached around the test optotype obj1. A light of the test optotype obj1 enters the hollow housing 10, the diverging lens 30 demagnifies the test optotype obj1, and generates a first virtual image img1 within a range of the converging focal length f2. The converging lens 20 magnifies the first virtual image img1 to form a second virtual image img2. An imaging height of the second virtual image img2 is similar to or equal to a height of the test optotype seen by the respondent at a distance of six meters in a general indoor vision test.

The higher the magnification of vision test apparatus 1, the difficulty of vision test will be increased, so it is necessary to set an appropriate magnification. In order to optimize a configuration of the system, and improve an effect of the visual acuity levels, the magnification of the converging lens 20 and the diverging lens 30 is 10~15; a length of the vision test apparatus is 190 mm-130 mm. According to a standard of Snellen Chart, the range of tested visual acuity levels from 1.6 to 0.05, and at least 15 tested visual acuity levels may be designed according to the needs. Further, the converging lens 20 is a plano-convex lens, the diverging lens 30 is a plano-concave lens, and a plane of the converging lens 20 and a concave surface of the diverging lens 30 are arranged to face each other, and are located in the hollow housing 10.

In order to be able to control a beam quality of a plurality of parallel rays generated by the converging lens 20 to meet a light level and a visual acuity level received by the eyeball of the respondent, a diaphragm 40 may be further set in the hollow housing 10. The diaphragm 40 is disposed between the converging lens 20 and the diverging lens 30, and adjacent to the converging lens 20. The diaphragm 40 is used to filter out an excess scattered or refracted light, so as to adjust an angle and quantity of the light entering the converging lens 20.

Figure 4:
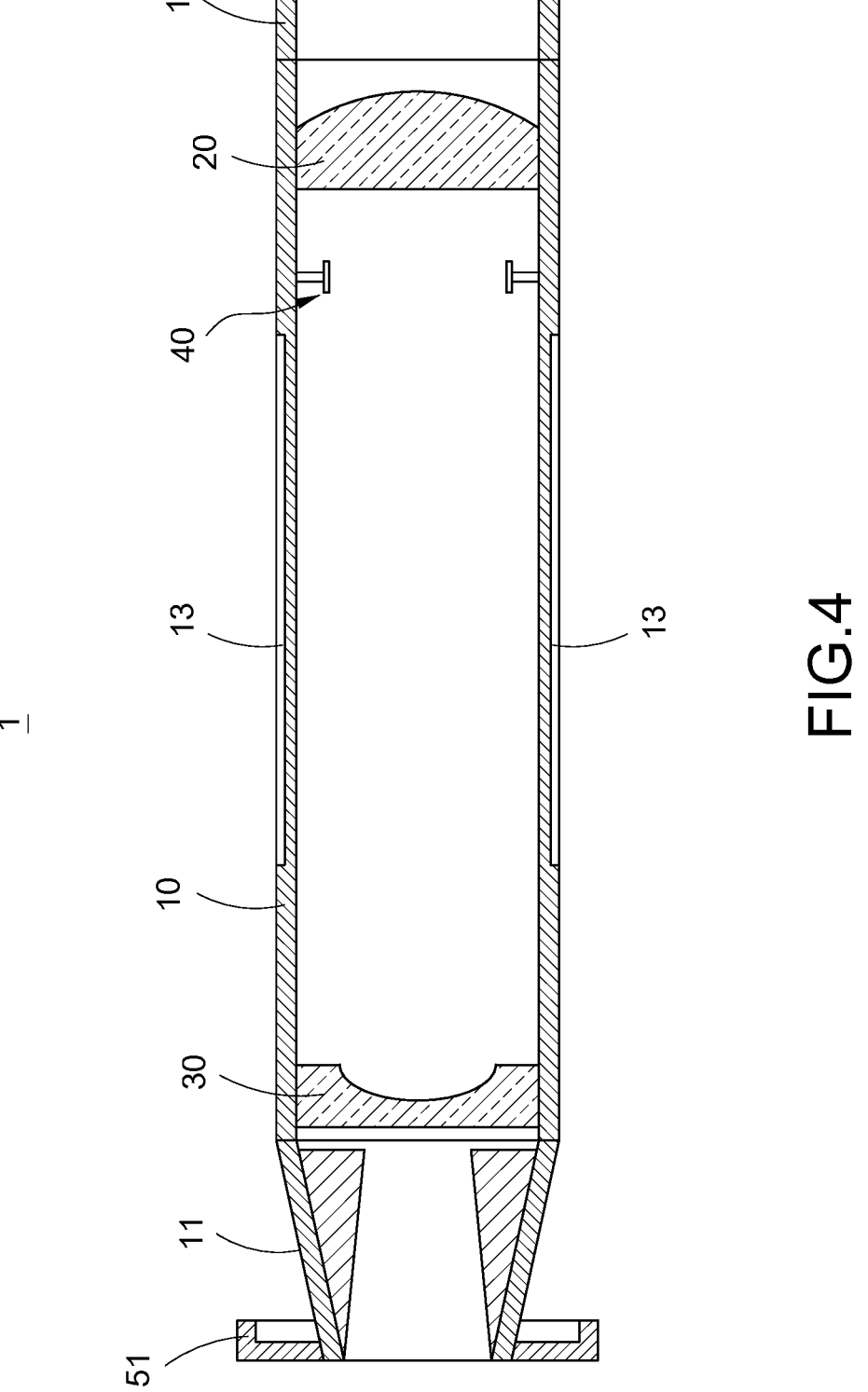
FIG. 4 is a schematic structural diagram of a second embodiment of the vision test apparatus of the present disclosure.

Please refer to FIG. 4, which is a schematic structural diagram of a second embodiment of the vision test apparatus of the present disclosure. The second embodiment of the present disclosure is similar to the first embodiment, but a periphery of the light shield 11 includes a hook structure 51. The hook structure 51 can use objects such as a rubber band or a belt to closely attaches the light shield 11 to the display apparatus 60 for displaying the test optotype obj1 (as shown in FIG. 1 and FIG. 2).

Figure 5:
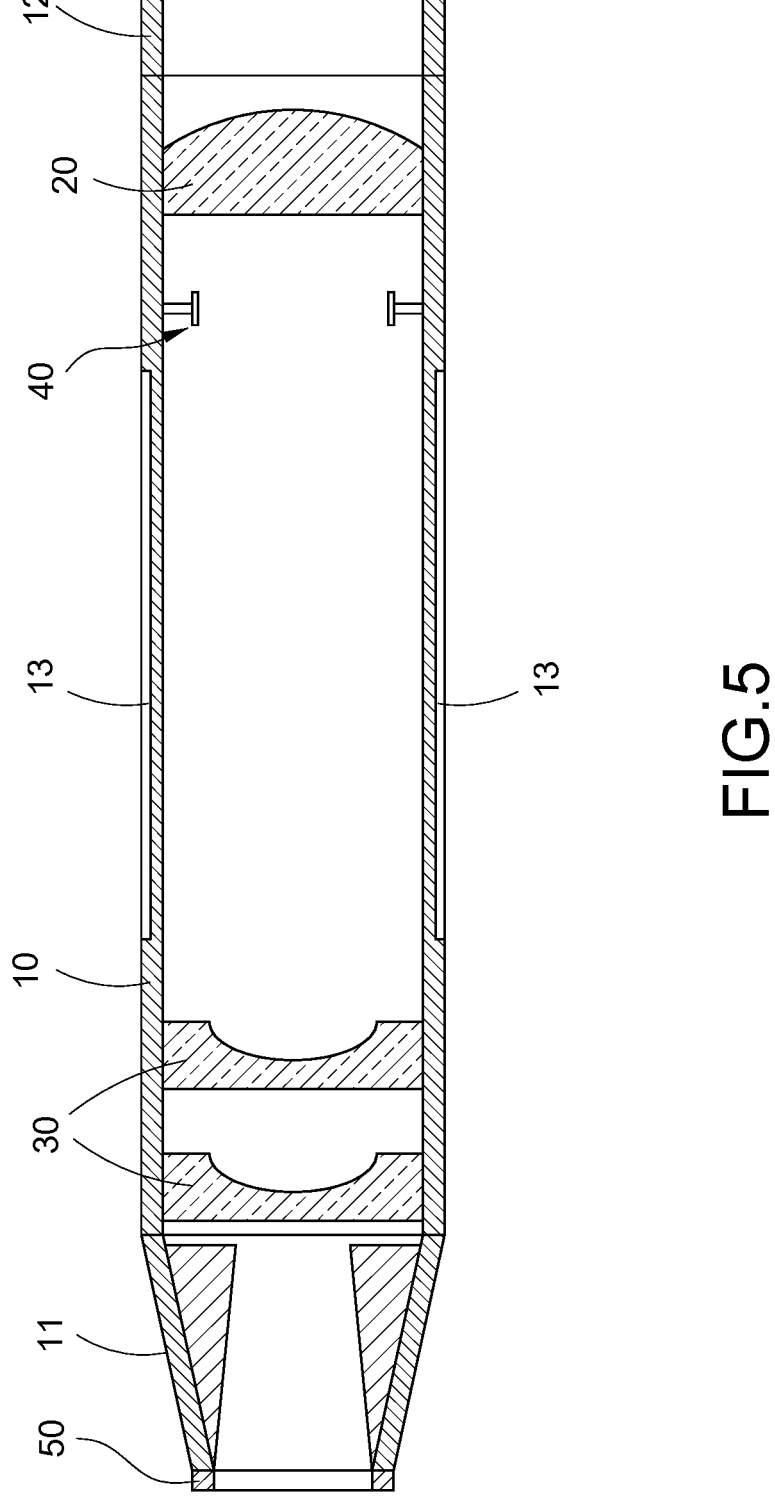
FIG. 5 is a schematic structural diagram of a third embodiment of the vision test apparatus of the present disclosure.

Please refer to FIG. 5, which is a schematic structural diagram of a third embodiment of the vision test apparatus of the present disclosure. The third embodiment of the present disclosure is similar to the first embodiment, but the vision test apparatus 1 includes a plurality of diverging lenses 30 disposed adjacent to each other and arranged at intervals, and the plurality of diverging lenses 30 may preferably be two. Each diverging lens 30 is the plano-concave lens, and the concave surfaces of the diverging lenses 30 all face the plane of the converging lens 20. If a curvature of a single diverging lens 30 is too large, it may cause barrel deformation or aberration of the first virtual image img1. At this time, it may reduce or improve the aforementioned problems by disposing two diverging lenses 30.

Figure 6:
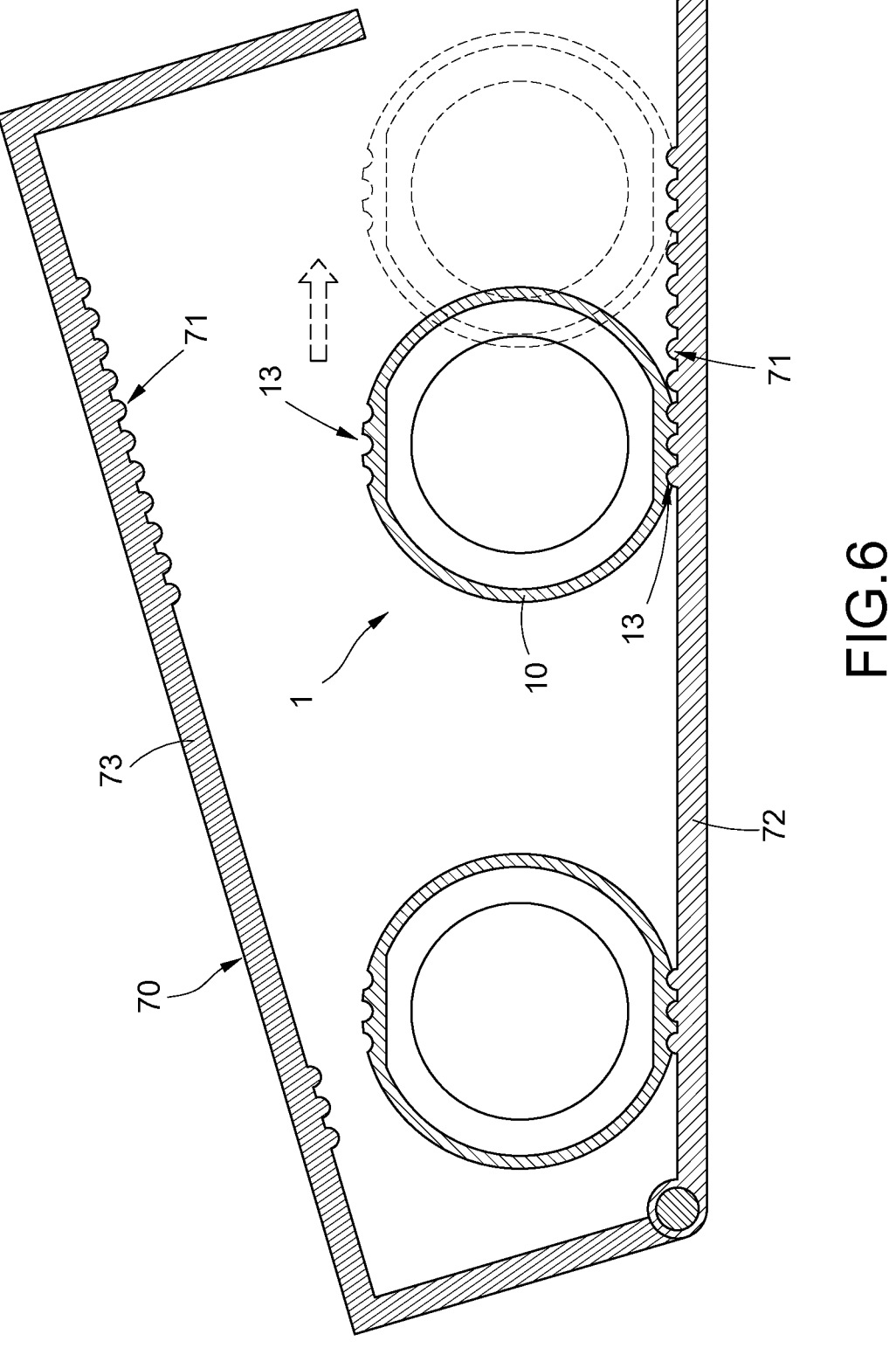
FIG. 6 is a schematic structural diagram of a binocular vision test apparatus of the present disclosure.

FIG. 6 is a schematic structural diagram of a binocular vision test apparatus of the present disclosure. The binocular vision test apparatus includes two vision test apparatuses 1 and an auxiliary frame 70. The binocular vision test apparatus is similar to the first to third embodiments, but a first clamping structure 13 is provided on the periphery of the hollow housing 10 of the vision test apparatus 1 of the present disclosure. The auxiliary frame 70 includes a second clamping structure 71. The auxiliary frame 70 engages with the first clamping structure 13 by the second clamping structure 71 to combine with the two vision test apparatuses 1.

In order to optimize an installation and match an inter-pupillary distance of the respondent, and facilitate adjustment of a distance between the two vision test apparatuses 1, in a specific embodiment, the first clamping structure 13 is a plurality of parallel grooves arranged on both sides of the hollow housing 10. The auxiliary frame 70 has a bottom plate 72 and an upper cover 73. The second clamping structure 71 is a plurality of parallel grooves respectively disposed on the bottom plate 72 and the inner side surface of the upper cover 73. When the auxiliary bracket 70 is to be combined with the two vision test apparatuses 1, the respondent adjusts the distance between the two vision test apparatuses 1 according to his own interpupillary distance configuration, one side of the vision test apparatuses 1 with the first clamping structure 13 is installed on the second clamping structure 71 of the bottom plate 72, and the parallel grooves between the vision test apparatuses 1 and the bottom plate 72 are engaged with each other. The second clamping structure 71 of the upper cover 73 is covered with the first clamping structure 13 on the other side of the vision test apparatus 1, so that the parallel grooves between the upper cover 73 and the vision test apparatus 1 are engaged with each other. The combination of the two vision test apparatus 1 is completed for simultaneous vision test of both eyes or other potential applications.

Please refer to FIG. 7, which is a schematic flowchart of a method of vision test of the present disclosure. The method of vision test cooperated with the vision test apparatus 1 to perform the vision testing, and the method includes the following steps: the display apparatus 60 performs an image processing on a base optotype with a predetermined pixel size by a scaling method, and the display apparatus 60 generates a plurality of test optotypes obj1 with sizes of integral multiple of a 5*5 pixel size and with sizes not divisible by the 5*5 pixel size, namely not integral multiple of a 5*5 pixel size (step S1); the display apparatus 60 performs an image compensation on the test optotypes obj1 with sizes not divisible by the 5*5 pixel size, so that the pixel size is between each test optotype obj1 with an arithmetic sequence relationship (step S2); the display apparatus 60 displays the corresponding test optotype obj1 according to a tested visual acuity level of a respondent (step S3); the vision test apparatus 60 attaches the test optotype obj1 to perform the vision test (step S4); and the display apparatus 60 receives a response message from the respondent, and performs a visual acuity level judgment (step S5).

Further, in step S3, before the display apparatus 60 displays the test optotype obj1, the respondent may be randomly selected from a preset visual acuity level such as 0.4 to 0.8 according to a preset way to start the test. In addition, the display apparatus 60 may also display the corresponding test optotype obj1 according to the visual acuity level set by the respondent to start a visual test. The visual acuity level is set according to their current physical condition or the results of a previous visual test, there is no need to start from scratch, which has a benefit of saving a test time for the respondent. Regarding a setting operation of the visual acuity level, the respondent performs the setting operation on the display apparatus 60 by himself, and may also achieve the same function through other electronic devices, there is no limited thereto.

In addition, during the visual test of the present disclosure, the display apparatus 60 displays the corresponding test optotype obj1 and executes the visual acuity level judgment. The respondent performs multiple visual acuity level judgments for different visual acuity levels, and each visual test corresponds to the different test optotypes obj1 for different visual acuity levels. The display apparatus 60 successively updates the second-round vision test level according to a correct response message of the respondent, until the visual test is completed. According to the last visual test, the corresponding vision test level that is according to the correct response message for the test optotype obj1 of the respondent is provided to the respondent.

Further, the base optotype is a standard 100*100 pixel size of the test optotype obj1 with a black stripe image on a white background. The display apparatus 60 performs the image processing on the base optotype by the scaling method, and generates the plurality of test optotypes obj1 with sizes of integral multiple of a 5*5 pixel size (such as 5*5, 10*10, 15*15 . . . 0.30*30). The display apparatus 60 performs the image compensation on the test optotypes obj1 with sizes not divisible by the 5*5 pixel size (such as 6*6, 7*7, 8*8 . . . 21*21 22*22, 23*23 . . . 29*29), so that the pixel size between each test optotype obj1 with an arithmetic sequence relationship.

Moreover, the image compensation is to adjust a transparency of each grid of the non-black stripe portion around the black stripe in the black stripe image. According to different background colors of the display apparatus 60, there will be different colors after the transparency is adjusted. If the background color is white, it may be close to gray after adjustment, there is no limited thereto. In addition, as an E-shaped pattern of the test optotype obj1 in the Snellen Chart, the 5*5 pixel size may be used as a design reference, and different pixel sizes may be adjusted according to different E-shaped patterns, there is no limited thereto.

Further, in order to optimize the effect of image compensation on the edge of the image, the display apparatus 60 may perform the image compensation on the test optotypes obj1 respectively by an interpolation algorithm, especially a bilinear interpolation algorithm.

In order to more effectively illustrate the image compensation of the present disclosure, please further refer to FIG. 8, which are test optotypes obj1 with 5*5 pixel size and 7*7 pixel size. The display apparatus 60 uses the bilinear interpolation algorithm to perform the image compensation by adjusting the transparency of the non-black stripe portion around the black stripe in the black stripe image on the white background, so the test optotype obj1 with 7*7 pixel size generated has a complete E-shaped pattern. Because the generation method of the test optotype obj1 with 5*5 pixel size is the same as this, it will not be repeated here.

The pixel sizes corresponding to tests optotype obj1 with progressively-increased levels are different. For example, a size of the test optotype obj1 corresponding to visual acuity level 0.9 is slightly larger than that of test optotype obj1 corresponding to visual acuity level 1.0 by 10%. For example, when the pixel size of the test optotype obj1 of visual acuity level 1.0 is defined as 5*5, the resulting pixel size of the test optotype obj1 of visual acuity level 0.9 is 5.5*5.5. However, the current display screen may not display an image with a pixel size including a decimal point such as 5.5*5.5.

In some embodiments, if the pixel size of test optotype obj1 corresponding to visual acuity level 1.0 is increased to 50*50, the pixel size of test optotype obj1 corresponding to visual acuity level 0.9 may be changed to 55*55, but this method may only be applied to high-resolution display screens, resulting in limited technical application. If the aforementioned pixel size specification is implemented in the vision test apparatus 1 of the present disclosure, the display screen will require the resolution about 2180 pixels/inch, which obviously does not meet the screen specifications of current electronic apparatuses. Therefore, the method of the image compensation of the present disclosure may effectively overcome this problem, and has an effect of being widely used in low-resolution display screens.

In some embodiments, the response message includes the respondent's voice, touch, touch sliding, etc., so that the display apparatus 60 perceives a respondent's answer to perform the visual acuity level judgment. The step S5 may further include reducing or eliminating a behavior that the respondent may guess, so as to avoid affecting the judgment of the visual acuity level. The display apparatus 60 further confirms whether to lower the visual acuity level according to receiving the response message and supplemented by the record data including the answering time and the answering error rate of the respondent (step S51); If confirmative, the display apparatus 60 displays the lowered visual acuity level (step S52); If not confirmative, the display apparatus 60 displays the calculated visual acuity level (step S53).

In particular, the aforementioned step S51 is that the display apparatus 60 first performs the step S5 to judge the visual acuity level according to the perceived response message, and then further performs comprehensive calculations according to recorded data such as the answering time and the answering error rate of the respondent. If the answering time is too short, too long, or the answering error rate is high, etc., it may be classified as the respondent who has made more guesses during the vision test, and then the judgment is "Yes". Meanwhile, it may actively downgrade the visual acuity level for one or more levels according to the result of the visual acuity level obtained in step S5, and provide the downgraded visual acuity level result to the respondent to know. If the judgment is "No", the result of the visual acuity level of the original step S5 is provided.

In some embodiment, the method of vision test may be presented in a program that is storage in a non-transitory computer-readable recording medium, the display apparatus 60 may install the non-transitory computer-readable recording medium to execute the program.

Therefore, the vision test apparatus 1, method, system, and non-transitory computer-readable recording medium disclosed in the present disclosure solve the problems of related art that require a fixed field, are inconvenient to carry, and may not easily and instantly know a changing trend of the visual acuity level at any time. The present disclosure achieves an object of not requiring the fixed field, being portable, and being able to know easily a changing trend of the visual acuity level at any time. Further, the vision test apparatus 1 may use a lower magnification and a suitable length of the hollow housing 10 to increase the range of tested visual acuity levels. In addition, image processing steps used in the method of vision test may be widely used in display apparatuses with low resolution.

What is claimed is:

1. A vision test apparatus comprising:

a hollow housing made of translucent or transparent materials, wherein the hollow housing is configured to allow external ambient light to pass therethrough to illuminate a test optotype when the vision test apparatus is attached to an external display apparatus;

a converging lens arranged in the hollow housing, and comprising a converging focal length;

a diverging lens arranged in the hollow housing at intervals relative to the converging lens, and comprising a diverging focal length; two optical axes of the diverging lens and the converging lens configured to overlap each other, and the diverging focal length configured to partially overlap the converging focal length, wherein a magnification of the converging lens and the diverging lens is between 10 and 15, a length of the vision test apparatus is between 190 mm and 130 mm, thereby a range of tested visual acuity levels of the vision test apparatus is increased and an effect of the tested visual acuity levels is improved;

a diaphragm arranged in the hollow housing between the converging lens and the diverging lens, and adjacent to the converging lens, wherein the diaphragm is configured to filter out an excess scattered or refracted light generated between the converging lens and the diverging lens; and a light shield connected to one end of the hollow housing, and adjacent to the diverging lens, the light shield comprising a tapered structure and tapered toward the diverging lens, wherein the light shield is configured to be attached to the external display apparatus, and wherein the light shield is used to eliminate reflected or refracted lights and to maintain a fixed distance between the diverging lens and the display screen of the external display apparatus;

wherein, one end of the hollow housing adjacent to the diverging lens is configured to receive a test optotype displayed by the external display apparatus, the diverging lens is configured to demagnify the test optotype to form a first virtual image within the converging focal length, and the converging lens is configured to magnify the first virtual image to form a second virtual image for a vision testing;

wherein, a periphery of an opening at one end of the light shield comprises any one of a silicone layer, an electrostatic glass sticker, and a chemical adhesive layer;

wherein, the first virtual image is located at the overlap of the converging focal length and the diverging focal length.

2. The vision test apparatus of claim 1, wherein, the converging lens is a plano-convex lens, the diverging lens is a plano-concave lens, and a plane of the converging lens and a concave surface of the diverging lens are arranged to face each other.

3. The vision test apparatus of claim 2, wherein a number of the diverging lenses is two, and the two diverging lenses are adjacent to each other and are arranged at intervals, each diverging lens is the plano-concave lens, and the concave surfaces of the diverging lenses all face the plane of the converging lens.

4. The vision test apparatus of claim 1, wherein, a periphery of the light shield comprises a structure for attaching the test optotype.

5. A vision test system comprising:

a vision test apparatus of claim 1; and an external display apparatus.

* * * * *